United States Patent [19]

Tangherlini et al.

[11] Patent Number: 4,754,771
[45] Date of Patent: Jul. 5, 1988

[54] APPARATUS FOR WASHING BEADS

[75] Inventors: Vincent C. Tangherlini, Carlsbad; Philip A. Levinson, San Diego; John Maguire, Mission Viejo; Luis R. Urquidi, Fountain Valley, all of Calif.

[73] Assignee: Hybritech Incorporated, San Diego, Calif.

[21] Appl. No.: 756,403

[22] Filed: Jul. 17, 1985

[51] Int. Cl.⁴ ............................................. B08B 3/02
[52] U.S. Cl. ........................... 134/102; 134/182; 15/302; 422/100
[58] Field of Search ............... 134/21, 25.4, 102, 22.1, 134/182; 15/302, 304; 422/100; 210/282, 283

[56] References Cited

U.S. PATENT DOCUMENTS

| | | | |
|---|---|---|---|
| 3,836,329 | 9/1974 | Jordan | 134/21 X |
| 3,916,924 | 11/1975 | McGowan | 134/102 X |
| 4,099,674 | 7/1918 | Standley | 239/431 |
| 4,106,155 | 8/1978 | Fosslien | 15/304 X |
| 4,398,382 | 8/1983 | Suovaniemi et al. | 53/431 |
| 4,472,204 | 9/1984 | Fishbach | 134/10 |
| 4,559,664 | 12/1985 | Bonme et al. | 15/302 |
| 4,611,553 | 9/1986 | Iwata et al. | 15/302 |

FOREIGN PATENT DOCUMENTS

| | | |
|---|---|---|
| 177517 | 1/1906 | Fed. Rep. of Germany . |
| 507273 | 9/1930 | Fed. Rep. of Germany . |
| 3122408 | 12/1982 | Fed. Rep. of Germany . |
| 3233079 | 3/1984 | Fed. Rep. of Germany . |
| 747211 | 3/1956 | United Kingdom . |

Primary Examiner—Harvey C. Hornsby
Assistant Examiner—Frankie L. Stinson
Attorney, Agent, or Firm—Lyon & Lyon

[57] ABSTRACT

An apparatus for washing and aspirating the wash solution from beads contained in receptacles. Adequate bead agitation and the washing of the entire bead surface is insured by use of a bearing surface at the interface between the bead and the apparatus.

4 Claims, 3 Drawing Sheets

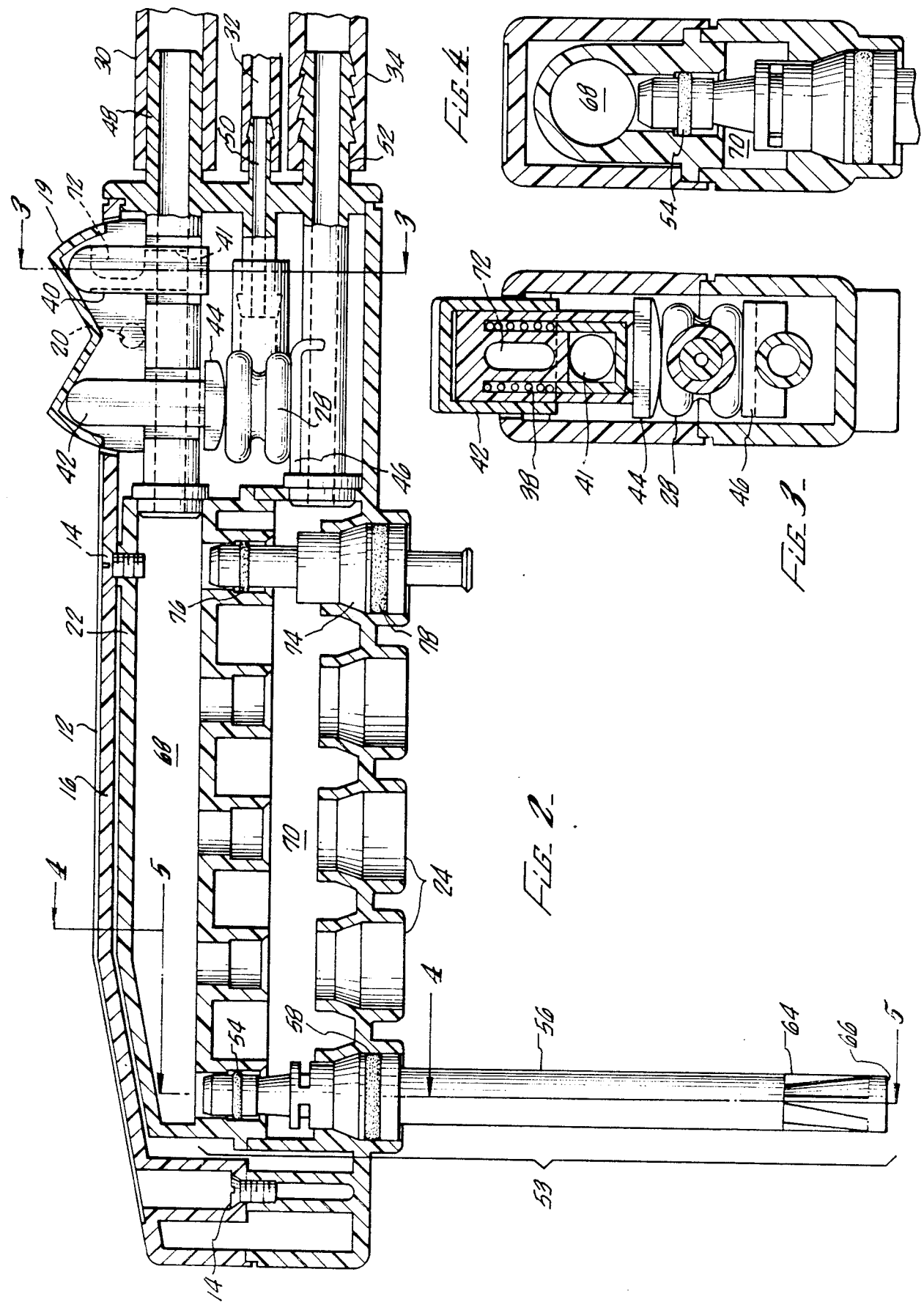

APPARATUS FOR WASHING BEADS

BACKGROUND OF THE INVENTION

The field of the present invention relates to washers used for washing and aspirating the wash solution from a solid body member.

Certain types of immunologic diagnostic assays require the use of solid supports (hereinafter referred to as "beads") as supports upon which certain chemical and/or bio-chemical reactions take place. Beads can be fashioned out of glass, metal or plastics.

Certain immunologic diagnostic assays are primarily directed to measuring the quantity of material that has reacted with the sample under test. It is frequently necessary while conducting such assays to completely wash and aspirate the wash solution from beads which are resident in reaction vessels, such as test tubes, in order to remove as completely as possible the excess material which has not reacted with the sample under test. The effectiveness of such washing can directly impact the accuracy and precision of such assays. In order to achieve a thorough washing of the bead, it is necessary to wash the entire surface of the bead.

Known bead washing systems aspirate excess washing fluid through an aperture at the center of the bottom portion of the probe. Thus, the bead is drawn into stable contact with the center of the bottom portion of the probe and at least some portion of the bead will be in relatively stable contact with the probe. Although these systems are fit for their intended purposes, a stable contact point with the bottom of the probe tends to hinder the washing effect at that point and in the area immediately surrounding it.

It is desirable to provide an improved system for washing beads used as solid supports in immunologic diagnostic assays that are capable of more completely washing such beads.

SUMMARY OF THE INVENTION

The present invention provides an apparatus for washing beads that avoids the above-noted and other disadvantages of known bead washing methods and devices. The invention holds the bead in unstable equilibrium at the bottom of the probe so that the bead may roll and spin around on the bottom surface of the probe exposing all of its surface to washing fluid.

In accordance with the invention, a probe comprising two passages may be lowered into a reaction vessel housing a bead. The first of said passages may be opeatively connected to a washing fluid source and the second of said passages may be operatively connected to a low pressure air source. Washing fluid may be delivered to the bead through the first of said passages. A bearing surface about the center line of the second of said passages including a plurality of ports extending through said bearing surface allows the bead to be drawn up to the bearing surface whereby it may freely move in unstable contact with the bearing surface while being agitated by the action of the wash solution being introduced into the vicinity of the probe by the first of said passages and the aspiration of the wash solution through said ports. The unstable equilibrium achieved by the bead effects more efficient washing of the bead.

Accordingly, it is an object of the present invention to provide a novel apparatus for washing beads used as solid supports in immunologic diagnostic assays. Other and further objects and advantages will appear hereinafter.

BRIEF DESCRIPTION OF THE DRAWINGS

FIG. 2 is a cross-sectional view of the head of the bead washer showing a single probe assembly in place and a single plug assembly in place.

FIG. 3 is a cross-sectional view taken along line 3—3 of FIG. 2.

FIG. 4 is a cross-sectional view taken along line 4—4 of FIG. 2.

DETAILED DESCRIPTION OF THE PREFERRED EMBODIMENT

The diagnostic assay bead washer has been designed to be a lightweight hand-held apparatus for simultaneously washing a plurality of beads used as solid supports for immunologic diagnostic assays each located in an individual receptacle. The body of the bead washer is fashioned from injection molded synthetic thermoplastics.

Figure 1:
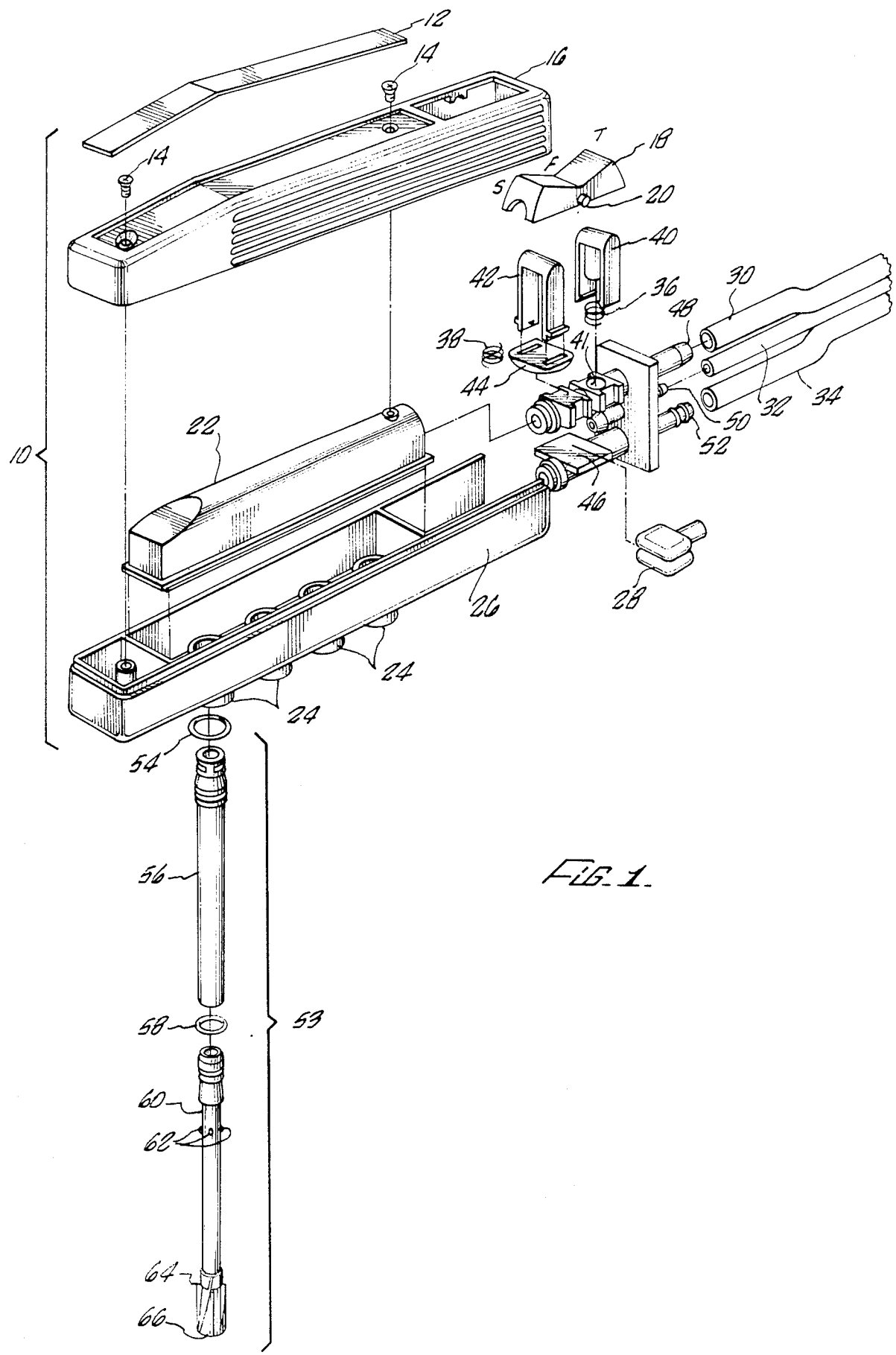
FIG. 1 is a perspective view of the head of the bead washer and a single probe assembly.

Turning in detail to the drawings, FIG. 1 illustrates a hand-held diagnostic bead washer and probe assembly 10 (hereinafter referred to as the "bead washer"). As can be seen from the figures, a single bead 82 (illustrated in FIG. 8) per receptacle can be washed when probe assembly 53 is lowered into the receptacle and rocker switch 18 is pivoted into its second switching position. This action forces flunger 42 and pad 44 downward compressing bellows 28 between pad 44 and surface 46 to effect an increase in pressure in control line 32 which is connected to the bead washer head at connector 50. Control line 32 is attached to a pressure switch (not shown) which, when a higher than normal pressure is available along control line 32, causes a pump (not shown) to cycle forcing a measured amount of washing fluid from a washing fluid source through washing fluid supply line 34. Washing fluid enters the bead washer head through connector 52. A low pressure air supply is connected to the bead washer head via low pressure air line 30 at connector 48. The low pressure air supply is distributed to the various probe assemblies with manifold 22. Washing fluid is distributed to the various probe assemblies with manifold 26. The removable probe assemblies 53 fit into the bead washer head at probe attachment points 24 with the inner probe assembly 60 which carries the low pressure air supply extending into the manifold 22 and sealed thereto with O-ring 58. Outer probe assembly 56 carries the washing fluid between its inner wall and the outer wall of inner probe assembly 60. The passage thereby defined 61 is sealed to the manifold 26 with O-ring 54. Proper spacing and registration between the inner and outer probe assemblies is aided by raised portions 62 of the inner probe assembly.

The top cover of the body 16 is attached to the body assembly 22, 26 with screws 14 and cover plate 12 covers the screws and may be used to note information.

Springs 38 and 36 act to bias rocker switch 18 to its neutral first position. Fins 64 may be used at the end of the probe assemblies to deflect washing fluid for improved washing action.

Turning in detail to FIG. 2, probe plug 74 may be utilized to seal an unused probe attachment point 24 so that the bead washer may be used with less than all of its probes. To utilize the option, probe assembly 53 is detached from the bead washer head and probe plug 74 is attached in its place. The probe plug consists of a piece of plastic or similar material closed at the top. The low pressure air supply manifold region 68 is sealed by O-ring 76 and the washing fluid supply manifold region 70 is sealed by O-ring 78. To replace the probe assembly, the probe plug is removed and a probe assembly inserted at the available probe attachment point.

Figure 5:
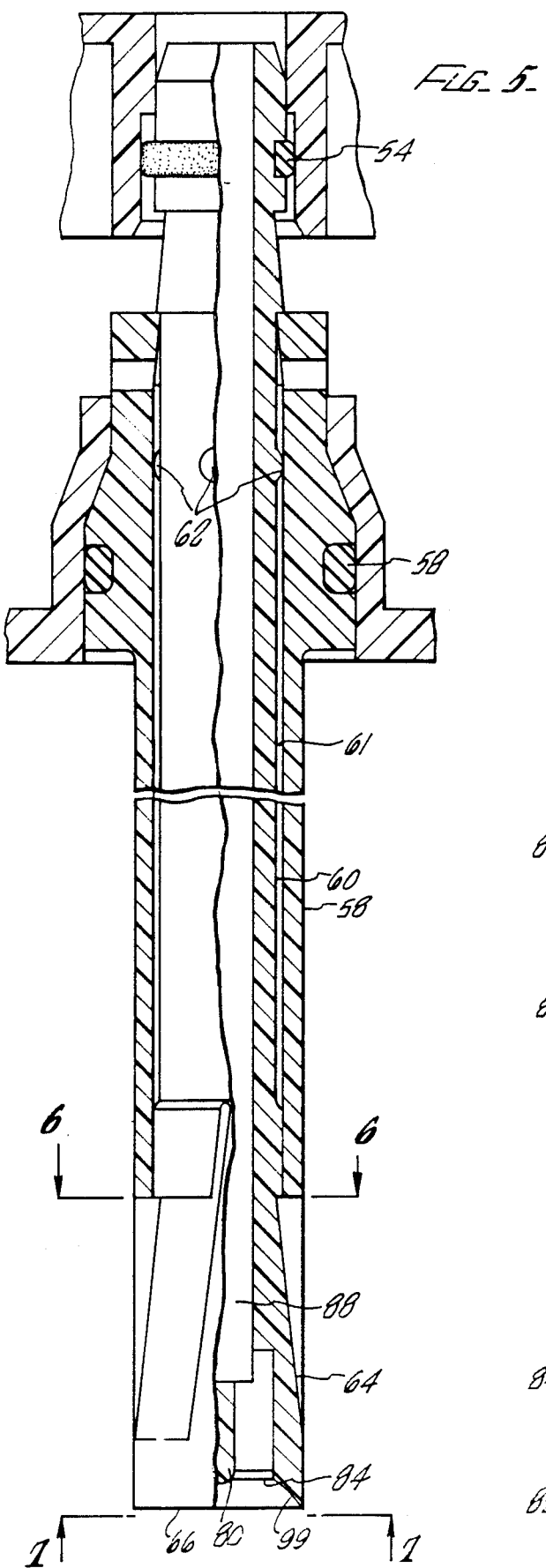
FIG. 5 is a partial sectional view of the probe assembly taken along line 5—5 of FIG. 2.
Figure 6:
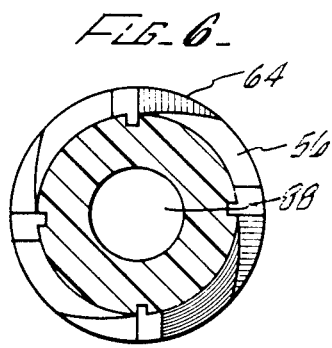
FIG. 6 is a cross-sectional view of the probe assembly taken along line 6—6 of FIG. 5.
Figure 7:
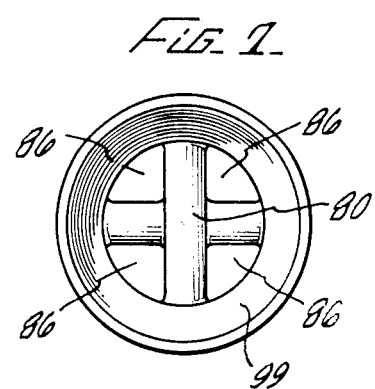
FIG. 7 is a bottom view of the probe assembly.
Figure 8:
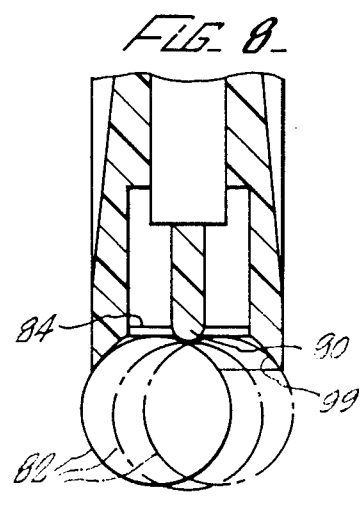
FIG. 8 is a cross-sectional view of the bottom of the probe assembly showing a bead in place throughout the range of its motion.

Turning now in detail to FIGS. 5, 7 and 8, agitation of the bead 82 is depicted in FIG. 8. The bead is free to move around on bearing surface 84. A raised portion 80 to the bearing surface may be provided to aid agitation and fluid flow through the ports. In an actual embodiment of the invention, the raised portion 80 was fabricated with dimensions that prohibited the bead from actually making contact with the unraised portion of the bearing surface and provided a clearance of approximately 0.020–0.030 inches therefrom. In this case, bead contact is confined to raised portion 80 of the bearing surface and conical surface 99. Fluid flowing around the bead and back through aspiration ports 86 causes additional bead agitation thereby insuring that the bead does not rest on any single point during the entire bead washing procedure. Fluid is drawn away from the bead through aspiration ports 85 and up low pressure air tube 88 at the core of the inner probe assembly.

When the bead washing procedure is completed, and the measured amount of washing fluid has washed the bead and been aspirated completely from the receptacle, the operator moves the rocker switch 18 to the third switching position depressing plunger 40 and blocking the low pressure air supply at hole 41 and causing the low pressure air supply to vent through elongated opening 72 (shown in FIG. 3). This action shuts off the low pressure air flow to the manifold 68 without tending to cause the low pressure air line 30 to collapse.

Improved agitation may be achieved by placing a port connecting the tip surface directly with the passage 61.

Thus, an apparatus for washing beads is disclosed which is useful for washing beads located in receptacles. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An apparatus for washing and for aspirating a washing fluid from an object within a receptacle comprising:
    a body operatively connected to both a low pressure air source and a washing fluid source;
    a probe having a first end and a second end,
    said first end of said probe being attached to said body and operatively connected to both said low pressure air source and said washing fluid source;
    said probe insertable into said receptacle;
    said second end of said probe including a tip surface adjacent said object having a substantially concave surface with a bearing surface normal to the centerline of said probe,
    said bearing surface having a plurality of ports therethrough;
    a solid raised portion at the center of said bearing surface; and
    means adjacent said second end of said probe for introducing said washing fluid into said receptacle and means contiguous with said tip surface for aspirating said washing fluid from said receptacle through said plurality of ports.

2. An apparatus for washing and for aspirating a washing fluid from an object within a receptacle comprising:
    a body operatively connected to both a low pressure air source and a washing fluid source;
    at least one probe having a first end and a second end, said first end of said probe being removable attached to said body at a probe attachment point and operatively connected to both said low pressure air source and said washing fluid source;
    said probe insertable into said receptacle;
    said second end of said probe including a tip surface adjacent said object having a substantially concave surface with a bearing surface normal to the centerline of said probe;
    said bearing surface having a plurality of ports therethrough;
    a solid raised portion at the center of said bearing surface; and
    means adjacent said second end of said probe for introducing said washing fluid into said receptacle and means contiguous with said tip surface for aspirating said washing fluid from said receptacle through said plurality of ports.

3. An apparatus for washing and for aspirating a washing fluid from an object within a receptacle comprising:
    a body operatively connected to both a low pressure air source and a washing fluid source;
    a plurality of probe attachment points;
    at least one probe having a first end and a second end, said first end of said probe being removably attached to said body at a probe attachment point and operatively connected to both said low pressure air source and said washing fluid source;
    said probe insertable into said receptacle;
    said second end of said probe including a tip surface adjacent said object having a substantially concave surface with a bearing surface normal to the centerline of said probe;
    said bearing surface having a plurality of ports therethrough;
    a solid raised portion at the center of said bearing surface; and
    means adjacent said second end of said probe for introducing said washing fluid into said receptacle and means contiguous with said tip surface for aspirating said washing fluid from said receptacle through said plurality of ports; and
    at least one probe plug removably attached to said body at an unused probe attachment point and independently sealing the low pressure air source and the washing fluid source at said unused probe attachment port.

4. An apparatus for washing and for aspirating a washing fluid from an object within a receptacle comprising:
   a body operatively connected to both a low pressure air source and a washing fluid source;
   at least one probe having a first end and a second end;
   said first end of said probe being operatively connected to both said low pressure air source and said washing fluid source;
   said probe insertable into said receptacle;
   said second end of said probe including a tip surface adjacent said object having a substantially concave surface with a bearing surface normal to the centerline of said probe;
   said bearing surface having a plurality of ports therethrough;
   a solid raised portion at the center of said bearing surface; and
   means adjacent said second end of said probe for introducing said washing fluid into said receptacle and means contiguous with said tip surface for aspirating said washing fluid from said receptacle through said plurality of ports.

* * * * *